United States Patent [19]

Chou

[11] 4,159,267

[45] Jun. 26, 1979

[54] NOVEL SILYL ESTER AZETIDINE-2-SULFENATE INTERMEDIATES AND PROCESS FOR PREPARING DESACETOXYCEPHALOSPORINS

[75] Inventor: Ta-Sen Chou, Indianapolis, Ind.

[73] Assignee: Eli Lilly and Company, Indianapolis, Ind.

[21] Appl. No.: 767,235

[22] Filed: Feb. 9, 1977

Related U.S. Application Data

[63] Continuation-in-part of Ser. No. 640,606, Dec. 15, 1975, abandoned, which is a continuation-in-part of Ser. No. 252,078, May 10, 1972, abandoned.

[51] Int. Cl.$^2$ .................. C07D 205/08; C07F 7/04; C07D 403/12; C07D 401/12
[52] U.S. Cl. .................. 260/239 A; 260/239.3 R; 260/307 A; 260/308 D; 260/326 E; 260/326.37; 260/332.2 H; 260/347.4; 260/345.8; 548/301; 546/208; 546/275; 544/18; 544/30
[58] Field of Search .................. 260/239 A, 239.3 R, 260/326 E, 326.37, 281 GN, 309.7, 345.8, 308 D, 260, 332.2 H, 347.2, 294.8 R

[56] References Cited

U.S. PATENT DOCUMENTS

| | | | |
|---|---|---|---|
| 3,275,626 | 9/1966 | Morin et al. | 260/243 C |
| 3,944,545 | 3/1976 | Chou | 260/239 A |

FOREIGN PATENT DOCUMENTS 799273  11/1973  Belgium.

OTHER PUBLICATIONS

Chou et al., J. Amer. Chem. Soc. 96, 1609 (1974).
Noyals, "Advanced Organic Chemistry", (Prentis-Hall 1954), pp. 412-414.
Zakharin et al., Chem. Abs. 56, 10177b (1961).
Chou II, Chem. Abs. 82, 170651y (1975).

*Primary Examiner*—Mark L. Berch
*Attorney, Agent, or Firm*—William C. Martens, Jr.; Arthur R. Whale

[57] ABSTRACT

A penicillin sulfoxide is heated in the presence of silylating agent to produce a novel silyl ester azetidine-2-sulfenate which, by treatment with acid, is converted to a desacetoxycephalosporin compound.

24 Claims, No Drawings

NOVEL SILYL ESTER AZETIDINE-2-SULFENATE INTERMEDIATES AND PROCESS FOR PREPARING DESACETOXYCEPHALOSPORINS

CROSS REFERENCE

This application is a continuation-in-part of application Ser. No. 640,606 filed Dec. 15, 1975, now abandoned, which is a continuation-in-part of application Ser. No. 252,078 filed May 10, 1972, and now abandoned.

BACKGROUND OF THE INVENTION

The semi-synthetic production of a 7-acylamidodesacetoxycephalosporin antibiotic from a penicillin starting material has been of exceptional importance since the advent of the invention of Morin and Jackson (U.S. Pat. No. 3,275,626) who describe and claim a process for converting a penicillin sulfoxide ester to a desacetoxycephalosporanic acid ester. Subsequently, improvements were made upon this Morin-Jackson process. Robin D. G. Cooper found that the use of certain tertiary carboxamide solvents (British Pat. No. 1,204,972) or certain tertiary sulfonamide solvents (British Pat. No. 1,204,394) directed the heat rearrangement of the penicillin sulfoxide esters more specifically toward production of the corresponding desacetoxycephalosporin esters and permitted the use of lower temperatures. Hatfield (U.S. Pat. No. 3,591,585) improved upon the Cooper contributions by finding that the conversion of a penicillin sulfoxide ester to a desacetoxycephalosporin ester by heating under acid conditions in the presence of a tertiary carboxamide solvent can be further improved by carrying out the reaction in the presence of both a sulfonic acid and means for removing or inactivating water present in the reaction mixture.

The mechanism which is postulated in U.S. Pat. No. 3,275,626 for the conversion of the penicillin sulfoxide ester to a desacetoxycephalosporanic acid ester is by formation of a sulfenic acid involving scission of the S-$C_2$ bond. This mechanism has now been conclusively established, and it furthermore has been shown (R. D. G. Cooper, J.A.C.S, 92, (1970) pp. 5010–5011) that, under the conditions of reaction, a thermal equilibrium between the sulfoxide starting material and the sulfenic acid intermediate is established. One approach which would be advantageous in accomplishing the desired conversion of a penicillin sulfoxide or ester derivative thereof to its corresponding desacetoxycephalosporanic acid or ester derivative would be to trap the fleeting and unstable sulfenic acid intermediate in the form of a stable and isolatable intermediate. This intermediate could then be isolated and subsequently converted to the corresponding desacetoxycephalosporin or could be formed under conditions which, without isolation, would permit a virtual immediate conversion to the corresponding desacetoxycephalosporin.

SUMMARY OF THE INVENTION

It is an object of this invention to provide compounds which are stable and isolatable intermediates in the conversion of penicillin sulfoxides or esters thereof to their corresponding desacetoxycephalosporanic acids or esters thereof.

It is also an object of this invention to provide a process for converting penicillin sulfoxides or esters thereof to their corresponding desacetoxycephalosporanic acids or esters thereof.

DETAILED DESCRIPTION OF THE INVENTION

Broadly, this invention relates to novel silyl ester compounds produced from penicillin sulfoxides. These silyl esters exhibit a sufficient degree of stability to render them isolatable and amenable to characterization. The silyl esters of this invention have the formula:

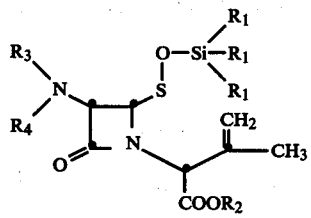

In the above formula the silicon atom is bonded to three groups characterized as $R_1$. Each $R_1$ independently is defined as $C_1$–$C_4$ alkyl or phenyl. $R_1$ preferably is methyl or phenyl and, most preferably, is methyl. Typical of the silyl radicals which can be present in the novel ester intermediates of this invention are trimethylsilyl, triphenylsilyl, methyldiethylsilyl, propyldimethylsilyl, and the like. Generically, the esters of this invention can be named as silyl esters of azetidine-2-sulfenates.

The group $R_2$ in the above formula is a carboxy protecting group. Such groups and their use are well known in the penicillin and cephalosporin arts and need no specific exemplification since the man skilled in the art is well aware of the large number of groups which are available. Preferred carboxy protecting groups include, for example, $C_1$–$C_6$ alkyl, 2,2,2-trihaloethyl, 2-iodoethyl, benzyl, nitrobenzyl, tetrahydropyranyl, 9-fluorenyl, succinimidomethyl, phthalimidomethyl, methoxybenzyl, dimethoxybenzyl, cyanomethyl, nitrophenyl, dinitrophenyl, 2,4,6-trinitrophenyl, bis(p-methoxyphenyl)methyl, triphenylmethyl, benzhydryl, benzyloxymethyl, $C_2$–$C_6$ alkanoyloxymethyl, $C_2$–$C_4$ alkanoyl, phenacyl, or a radical of the formula

in which each $R_1$ is as defined hereinabove, and the like.

Especially preferred carboxy protecting groups include $C_1$–$C_6$ alkyl, 2,2,2-trihaloethyl, benzyl, nitrobenzyl, methoxybenzyl, benzhydryl, $C_2$–$C_6$ alkanoyloxymethyl, phenacyl, or a radical of the formula

in which $R_1$ is methyl or phenyl.

In the above formula, $R_3$ and $R_4$ denote an amino protecting group. Such groups and their use are now well recognized in the penicillin and cephalosporin art and need no specific exemplification. Preferred amino protecting groups include, for example, the combination of $R_3$ being hydrogen and $R_4$ being $C_1$–$C_8$ alkanoyl; azidoacetyl; cyanoacetyl; haloacetyl;

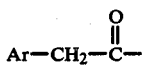

in which Ar is phenyl, thienyl, furyl, pyrrolyl, or phenyl substituted with from one to three substituents selected from the group consisting of fluorine, chlorine, bromine, iodine, trifluoromethyl, $C_1$–$C_3$ acyloxy, -OSi($R_1$)$_3$, $C_1$–$C_3$ alkyl, $C_1$–$C_3$ alkoxy, cyano, and nitro;

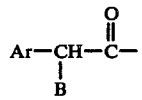

in which Ar' is phenyl, pyridyl, or substituted phenyl as defined above, and Y is oxygen or sulfur;

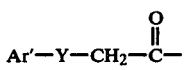

in which Ar is as defined above, and B is $C_1$–$C_3$ acyloxy,

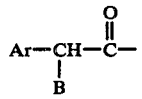

esterified carboxyl, -CN, -N$_3$, or -NHR in which R is benzyloxycarbonyl, $C_1$–$C_4$ alkoxycarbonyl, cycloalkoxycarbonyl, triphenylmethyl,

2,2,2-trichloroethoxycarbonyl, or -Si($R_1$)$_3$ in which $R_1$ is as herein defined; (3-sydnone)$C_2$–$C_3$ alkanoyl;

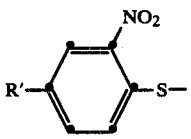

in which R' is hydrogen or methoxy; 2-(1H-tetrazol-1-yl)acetyl; and the like. Additional preferred amino protecting groups are those defined by $R_3$ and $R_4$ taken together with the nitrogen atom to which they are bonded, and include, for example, phthalimido, a cyclic imide moiety of a $C_3$–$C_{12}$ dicarboxylic acid, 2,2-dimethyl-5-oxo-4-phenylimidazolidin-1-yl, or the like.

More preferred amino protecting groups include those in which $R_3$ is hydrogen and $R_4$ is

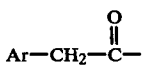

in which Ar is phenyl, thienyl, or phenyl substituted with from one to three substituents selected from the group consisting of fluorine, chlorine, bromine, iodine, trifluoromethyl, $C_1$–$C_3$ acyloxy, -OSi($R_1$)$_3$, $C_1$–$C_3$ alkyl, $C_1$–$C_3$ alkoxy, cyano, and nitro;

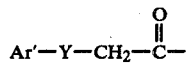

in which Ar' is phenyl, or substituted phenyl as defined above, and Y is oxygen or sulfur;

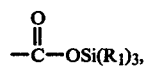

in which Ar is as defined above, and B is $C_1$–$C_3$ acyloxy,

or -NHR in which R is benzyloxycarbonyl, $C_1$–$C_4$ alkoxycarbonyl, cycloalkoxycarbonyl, triphenylmethyl,

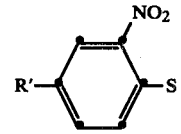

2,2,2-trichloroethoxycarbonyl, or -Si($R_1$)$_3$ in which $R_1$ is as herein defined;

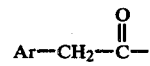

in which R' is hydrogen or methoxy; 2-(1H-tetrazol-1-yl)acetyl; or $R_3$ and $R_4$ taken together with the nitrogen atom to which they are bonded are phthalimido or 2,2-dimethyl-5-oxo-4-phenylimidazolidin-1-yl.

Especially preferred amino protecting groups include those in which $R_3$ is hydrogen and $R_4$ is

in which Ar is phenyl;

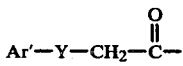

in which Ar' is phenyl, and Y is oxygen; or $R_3$ and $R_4$ taken together with the nitrogen atom to which they are bonded are 2,2-dimethyl-5-oxo-4-phenylimidazolidin-1-yl.

The novel silyl esters described above are intermediates in the conversion of penicillin sulfoxides to desacetoxycephalosporins. As has been developed in detail in Morin et al., *Journal of the American Chemical Society*, 91, (1969) pp. 1401–1407, ring expansion of penicillins to cephalosporins involves an oxidative cleavage of the $C_2$-sulfur bond producing a labile sulfenic acid intermediate having a double bond at the $C_2$ carbon. This intermediate is subsequently ring closed to achieve a 3- cephem cephalosporin. Due to the equilibrium characteristics of the reaction as it bears on the sulfenic acid intermediate, it is possible for the sulfenic acid to ring close to the 3-cephem cephalosporin or to revert to the penicillin structure. Therefore, it is highly desirable to trap the sulfenic acid intermediate in the form of a stable derivative which can then be further reacted to achieve the desired cephalosporin product. It is precisely such a process which is defined as another aspect of this invention.

This invention relates to a process for converting a penicillin sulfoxide to a desacetoxycephalosporin by heating the penicillin sulfoxide in an inert, substantially anhydrous solvent to a temperature of from about 75° C. to about 150° C. in the presence of a silylating agent and simultaneously or subsequently treating the reaction mixture in an acidic medium.

The process of this invention is distinguishable from prior uses of silicon-containing compounds in conjunction with penicillin sulfoxides. Gutowski, *Tetrahedron Letters*, 21, (1970) pp. 1779–1782, describes the epimerization of penicillin sulfoxide esters when exposed to a silylating agent at room temperature for several days. Belgian Pat. No. 763,104 teaches a process for reacting a penicillin sulfoxide by heating the sulfoxide to a temperature below 160° C. in an anhydrous medium and in the presence of a compound containing silicon and halogen and at least one nitrogenous base present in a quantity of at least 5 moles per mole of the sulfoxide.

In the process of this invention any silylating agent can be employed which will achieve the silylation of the sulfenic acid intermediate formed by thermal cleavage of the penicilin sulfoxide. Any such silylating agent will contain at least one moiety having the formula -Si($R_1$)3 in which $R_1$ is as herein defined, and, furthermore, such moiety will be so situated in the silylating agent molecule as to be readily cleavable therefrom under the conditions of reaction and thereby available for forming the azetidine-2-sulfenate silyl ester. Mixtures of silylating agents can likewise be employed. Preferably, any mixture of silylating agents will be such that each silylating agent will give rise to the same silyl protecting group. Preferred silylating agents include those having the following formulae:

(a)

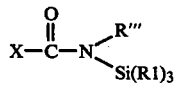

in which each $R_1$ independently is $C_1$–$C_4$ alkyl or phenyl, R''' is hydrogen, $C_1$–$C_4$ alkyl, or phenyl, and X is

in which J is hydrogen or -Si($R_1$)3, or X is -CW3 in which each W independently is hydrogen, trifluoromethyl, or $C_1$–$C_3$ alkyl;

(b)

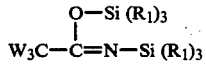

in which $R_1$ and W are as herein defined; and (c) Z-Si($R_1$)3 in which $R_1$ is as herein defined and Z is halogen, $C_2$–$C_3$ alkenyloxy, $C_1$–$C_3$ alkyl-SO3-, -O-Si($R_1$)3, -S-Si($R_1$)3, or

in which $R_5$ is hydrogen or $C_1$–$C_3$ alkyl, and $R_6$ is $C_1$–$C_4$ alkyl or -Si($R_1$)3, or $R_5$ and $R_6$ taken together with the nitrogen atom to which they are bonded form a heterocyclic ring having 5 or 6 atoms, up to 3 of which, in addition to the already-defined nitrogen atom, independently are nitrogen, sulfur, or oxygen.

Typical examples of the silylating agents which can be employed in the process of this invention include: N,O-bis(trimethylsilyl)acetamide, N,O-bis(triethylsilyl)acetamide, N,O-bis(triphenylsilyl)acetamide, N,O-bis(trimethylsilyl)trifluoroacetamide, N,O-bis(tripropylsilyl)trifluoroacetamide, N,O-bis(triphenylsilyl)trifluoroacetamide, N-trimethylsilylacetamide, N-tributylsilylacetamide, N-triphenylsilylacetamide, N-methyl-N-trimethylsilylacetamide, N-ethyl-N-triethylsilylacetamide, N-methyl-N-triphenylsilylacetamide, N-trimethylsilyl-N,N'-diphenylurea, N-triethylsilyl-N,N'-diphenylurea, N-triphenylsilyl-N,N'-diphenylurea, propenoxytrimethylsilane, ethenoxytriethylsilane, propenoxytriphenylsilane, trimethylsilyl methane sulfonate, tripropylsilyl ethane sulfonate, triphenylsilyl propane sulfonate, trimethylchlorosilane, triethylchlorosilane, triphenylchlorosilane, hexamethyldisilazane, hexaethyldisilazane, hexaphenyldisilazene, N-trimethylsilyl-t-butylamine, N-tripropylsilyl-t-butylamine, N-triphenylsilyl-t-butylamine, N-trimethylsilyldiethylamine, N-triethylsilyldimethylamine, N-triphenylsilylmethylethylamine, N-trimethylsilylimidazole, N-triethylsilylimidazole, a-triphenylsilylimidazole, hexamethyldisiloxane, hexapropyldisiloxane, hexaphenyldisiloxane, hexamethyldisilthiane, hexaethyldisilthiane, hexaphenyldisilthiane, and the like.

The conversion of the penicillin sulfoxide in accordance with the process of this invention is accomplished by heating the sulfoxide with the chosen silylating agent to a temperature of from about 75° C. to about 150° C. The heating of the sulfoxide is carried out in the presence of an appropriate inert, substantially anhydrous solvent. Any solvent can be employed which is inert to the penicillin sulfoxide and to the silylating agent and which has a sufficiently elevated boiling point to achieve the necessary reaction temperature. Suitable solvents include benzene, toluene, acetonitrile, dioxane, dimethylformamide, dimethylacetamide, and the like. Mixtures of appropriate solvents can also be employed.

The reaction mixture containing the penicillin sulfoxide is heated in the presence of a silylating agent at a temperature within the above range for a period necessary to effect conversion. This period can be very short or somewhat longer depending upon the reactants which are employed. Generally, the mixture will be heated for a period of from about 0.5 hours to about 24 hours. It is believed that the application of heat to the sulfoxide accomplishes a scission of the sulfur-$C_2$ bond. The scission of the sulfur-$C_2$ bond gives rise to a sulfenic acid type intermediate which is susceptible to attack by the silylating agent. The attack by the silylating agent traps the intermediate by production of a stable silyl ester having the structure of the class of novel intermediates of this invention.

Since one silyl moiety is required for each sulfenic acid moiety, at least an equimolar ratio of silylating agent to penicillin sulfoxide generally will be necessary. Certain silylating agents are so structured as to generate two or more silyl moieties per molecular. Correspondingly lesser molar quantities of such silylating agents can be employed. Generally, an excess of from about 1.1 to about 4 equivalents of the silylating agent will be employed per equivalent of the penicillin sulfoxide. Correspondingly, and as will be developed in detail hereinafter, certain penicillin sulfoxide starting materials will have additional points at which silylation can occur. In such instances one additional equivalent of the silyl moiety will be required for each such point of silylation.

In preparing the silyl ester intermediate of this invention, any of the above-mentioned silylating agents can be employed. However, strongly alkaline conditions must be avoided, or cleavage of the β-lactam ring will occur. Therefore, special precautions must be observed in those instances in which a silazane is employed as silylating agent. Since the use of a silazane results in the concomitant production of ammonia during silylation, care must be exercised to assure the immediate neutralization of the ammonia thus produced. This can be accomplished by including in the reaction mixture a minor amount of an acid which inactivates the ammonia upon its generation. A like result can be achieved by employing a combination of the silazane and a halosilane as silylating agent. The halosilane will generate a hydrogen halide as by-product of the silyl ester formation, and the hydrogen halide, in turn, will scavenge the ammonia generated from the silazane.

Conversely, care must be exercised in employing a halosilane as silylating agent. Since a hydrogen halide is formed during such silylation, the acidic conditions thereby developed may cause ring closure immediately to occur. In order to avoid this possibility, it is preferred to employ a mixture of silylating agents containing a sufficient amount of a silazane to neutralize by ammonia formation the hydrogen halide which forms.

The silyl ester intermediate either can be isolated from the silylation reaction mixture, or the silylation reaction mixture can be subjected to acid treatment to achieve ring closure of the silyl ester. Alternatively, the acid can be included with the penicillin sulfoxide in the reaction mixture at the outset of the reaction. Under the latter set of reaction conditions, the silyl ester intermediate will be transient, and ring closure with decomposition of the silyl ester will occur substantially simultaneously with the formation of the silyl ester.

Various acids can be employed in the ring closure portion of the process of this invention. Examples of suitable acids include sulfuric acid, phosphoric acid, and other mineral acids; methanesulfonic acid, p-toluenesulfonic acid, benzenesulfonic acid, naphthalenesulfonic acid, and other sulfonic acids; boron trifluoride, ferric chloride, aluminum chloride, and other Lewis acids; and other commonly recognized acidic reagents.

Highly preferred acids are sulfonic acids. Examples of preferred sulfonic acids are the $C_1$ to $C_{12}$-hydrocarbonsulfonic acids such as the $C_1$ to $C_{12}$-alkanesulfonic acids such as methanesulfonic acid, ethanesulfonic acid, hexanesulfonic acids, nonanesulfonic acids, dodecanesulfonic acids, and the like, as well as the $C_4$ to $C_7$-cycloalkanesulfonic acids such as cyclobutanesulfonic acid, cyclopentanesulfonic acid, cyclohexanesulfonic acid, and cycloheptanesulfonic acid, the $C_6$ to $C_{12}$ aryl- and alkarylsulfonic acids such as benzenesulfonic acid, dodecylbenzenesulfonic acids, alpha- and beta- naphthalenesulfonic acids, biphenylsulfonic acids, p-toluenesulfonic acid, xylenesulfonic acids, and the like, disulfonic acids such as methanedisulfonic acid, benzenedisulfonic acid, and the like, benzenetrisulfonic acid, mixtures of sulfonic acids, and such sulfonic acids substituted with groups that do not interfere with the ring closure reaction, such as chlorine, bromine, nitro, cyano, and the like, exemplified by p-chlorobenzenesulfonic acid, 3,5-dibromobenzenesulfonic acid, 4-nitroalpha-naphthalenesulfonic acid, and 4-cyanobenzenesulfonic acid. For economic reasons, the preferred sulfonic acids are $C_1$ to $C_6$-alkanesulfonic acids such as methanesulfonic acid, ethanesulfonic acid, and the simple $C_6$ to $C_8$ aryl and alkaryl hydrocarbonsulfonic acids such as benzenesulfonic acid, p-toluenesulfonic acid, and the like.

The acidic substance can be employed in a wide range of proportions relative to the silyl ester intermediate. In general, the molar ratio of the silyl ester intermediate to the acidic substance will be from 1:1 to about 100:1. Preferably, a molar ratio of the silyl ester intermediate to the acid ranges from about 5:1 to about 15:1. The concentration of the silyl ester intermediate in the total solvent system can vary extensively, but preferably the silyl ester intermediate constitutes from about 1 to about 20 percent by weight of the reaction mixture.

Preferably, the penicillin sulfoxide which is employed in the process of this invention is one having the formula

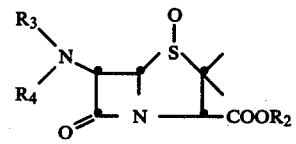

in which $R_3$ is hydrogen and $R_4$ is hydrogen; $C_1$–$C_8$ alkanoyl; azidoacetyl; cyanoacetyl; haloacetyl;

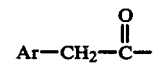

in which Ar is phenyl, thienyl, furyl, pyrrolyl, or phenyl substituted with from one to three substituents selected from the group consisting of fluorine, chlorine, bromine, iodine, trifluoromethyl, $C_1$–$C_3$ acyloxy, hydroxy, $C_1$–$C_3$ alkyl, $C_1$–$C_3$ alkoxy, cyano, and nitro;

in which Ar' is phenyl, pyridyl, or substituted phenyl as defined above, and Y is oxygen or sulfur;

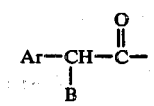

in which Ar is as defined above, and B is $C_1$–$C_3$ acyloxy, hydroxyl, carboxyl, esterified carboxyl, -CN, -$N_3$, -$NH_2$, or -NHR in which R is benzyloxycarbonyl, $C_1$–$C_4$ alkoxycarbonyl, cycloalkoxycarbonyl, triphenylmethyl,

or 2,2,2-trichloroethoxycarbonyl; (3-sydnone)$C_2$–$C_3$ alkanoyl;

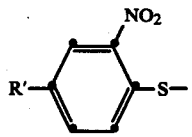

in which R' is hydrogen or methoxy; 2-(1H-tetrazol-1-yl)acetyl; or $R_3$ and $R_4$ taken together with the nitrogen atom to which they are bonded are phthalimido, a cyclic imide moiety of a $C_3$–$C_{12}$ dicarboxylic acid, or 2,2-dimethyl-5-oxo-4-phenylimidazolidin-1-yl; and $R_2$ is hydrogen, $C_1$–$C_6$ alkyl, 2,2,2-trihaloethyl, 2-iodoethyl, benzyl, nitrobenzyl, tetrahydropyranyl, 9-fluorenyl, succinimidomethyl, phthalimidomethyl, methoxybenzyl, dimethoxybenzyl, cyanomethyl, nitrophenyl, dinitrophenyl, 2,4,6-trinitrophenyl, bis(p-methoxyphenyl)methyl, triphenylmethyl, benzhydryl, benzyloxymethyl, $C_2$–$C_6$ alkanoyloxymethyl, $C_2$–$C_4$ alkanoyl, phenacyl, or a radical of the formula

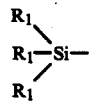

in which each $R_1$ independently is $C_1$–$C_4$ alkyl or phenyl.

The above definitions for $R_2$, $R_3$ and $R_4$ represent only a portion of the groups now well recognized in the penicillin and cephalosporin arts. Penicillin sulfoxides containing any of these well known substituents can be readily employed in the ring expansion process of this invention.

As mentioned above, it is contemplated by this invention to employ as starting material the sulfoxide of 6-aminopenicillanic acid (6-APA):

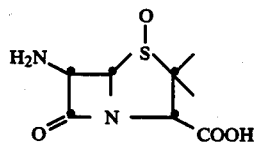

When the above is employed, three points of silylation exist. In accordance with the process of this invention, the stable silyl intermediate which will result during the thermal cleavage will have the formula

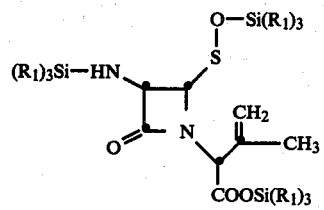

Thus, inherent in the process of this invention is the generation from 6-APA of a silyl ester intermediate having both the amino and the carboxy moieties suitably protected. Under the acidic conditions at which ring closure is accomplished to produce the desacetoxycephalosporin, both additional silyl protecting groups will be cleaved to produce the highly desirable 7-aminodesacetoxycephalosporanic acid (7-ADCA). The process of this invention thus permits the direct conversion of 6-APA sulfoxide to 7-ADCA. As will be apparent under the conditions of this specific conversion, it is essential that the ratio of silylating agent to 6-APA sulfoxide be such as will afford a minimum of three silyl moieties per each molecule of 6-APA sulfoxide.

It is correspondingly possible to employ as starting material a penicillin sulfoxide which has either a free amino function in the 6-position or a free carboxy function in the 3-position. In such instances the ratio of silylating agent to penicillin sulfoxide will be such as will afford a minimum of two silyl moieties per each molecule of the sulfoxide.

When $R_3$ of the sulfoxide starting material is hydrogen $R_4$ can be hydrogen or a silyl protecting group, such as trimethylsilyl, triethylsilyl, and the like. When $R_3$ and $R_4$ are each hydrogen, the resulting silyl ester intermediate which is produced will have one of the hydrogens replaced by the silyl protecting group. When $R_4$ of the sulfoxide starting material is a silyl protecting group, such silyl protecting group will be retained in the silyl ester intermediate. Upon ring-closure to form the desacetoxycephalosporin product, any silyl group which would have been present at the 7-amino function will be cleaved to produce a cephalosporin in which $R_3$ and $R_4$ are both hydrogen.

Representative of the silyl ester intermediates of this invention as well as the penicillin sulfoxides which can be used in and the desacetoxycephalosporins which can be prepared by the process of this invention are those in which $R_2$ is, for example, methyl, ethyl, n-propyl, isopropyl, n-butyl, sec-butyl, isobutyl, t-butyl, amyl, hexyl, 2,2,2-trichloroethyl, 2,2,2-tribromoethyl, 2-iodoethyl, benzyl, p-nitrobenzyl, tetrahydropyranyl, succinimidomethyl, phthalimidomethyl, p-methoxybenzyl, cyanomethyl, 3,4-dimethoxybenzyl, p-nitrophenyl, 2,4-dinitrophenyl, 2,4,6-trinitrophenyl, bis(p-methoxyphenyl)methyl, triphenylmethyl, benzhydryl, benzyloxymethyl, acetoxymethyl, propionoxymethyl, acetyl, propionyl, phenacyl, and the like.

$R_2$ of the sulfoxide starting material can also be hydrogen or a silyl protecting group, such as trimethylsilyl, triethylsilyl, triphenylsilyl, and the like. When such a starting material is employed, the silyl ester intermediate which is produced will be appropriately silylated in its carboxyl function. In the instance in which $R_2$ of the sulfoxide is hydrogen the carboxyl function of the silyl ester intermediate will be protected with the silyl group of the silylating agent which has been employed. In the instance in which $R_2$ of the sulfoxide is itself a silyl protecting group, such group will be retained in the silyl ester intermediate. Upon treatment of this silyl ester intermediate with acid to produce ring-closure, the silyl group which protects the carboxyl function can additionally be cleaved to produce the corresponding free acid cephalosporin.

Of the above, those $R_2$ groups which are highly preferred include t-butyl, 2,2,2-trichloroethyl, p-nitrobenzyl, benzyl, p-methoxybenzyl, benzhydryl, and trimethylsilyl.

The amino group of the penicillin sulfoxides which are used in and the desacetoxycephalosporins which are prepared by the process of this invention can incorporate any of a broad range of substituents. Representative examples of the $R_4$ substituent when $R_3$ is hydrogen include the following: formyl, acetyl, propionyl, butyryl, valeryl, caproyl, azidoacetyl, cyanoacetyl, chloroacetyl, bromoacetyl, phenylacetyl, 2-thienylacetyl, 3-thienylacetyl, 2-furylacetyl, 3-furylacetyl, 2-pyrrolylacetyl, 3-pyrrolylacetyl, 4-chlorophenylacetyl, 3-trifluoromethylphenylacetyl, 4-hydroxyphenylacetyl, 3-tolylacetyl, 4-cumylacetyl, 4-methoxyphenylacetyl, 3-cyanophenylacetyl, 4-nitrophenylacetyl, phenoxyacetyl, thiophenylacetyl, pyridyloxyacetyl, p-nitrophenoxyacetyl, α-aminophenylacetyl, α-benzyloxycarbamidophenylacetyl, α-t-butoxycarbamidophenylacetyl, α-formyloxyphenylacetyl, α-cyanophenylacetyl, α-azidophenylacetyl, 3-sydnoneacetyl, 2-(1H-tetrazol-1-yl)acetyl, 2-nitrophenylthio, 2-nitro-4-methoxyphenylthio, and the like. These as well as many other groups are now well recognized in the art.

Of the above $R_4$ substituents, those which are higly preferred include phenylacetyl, 2-thienylacetyl, and phenoxyacetyl.

The silyl ester intermediates of this invention can likewise contain any of the above substituents as well as many others, with the exception, however, that a reactive functional group which may be present in the $R_2$, $R_3$ or $R_4$ substituent of the penicillin sulfoxide may become silylated during formation of the intermediate. Upon ring closure of the thus-formed silyl ester intermediate to produce the desacetoxycephalosporin, the addition silyl group will be cleaved to generate a cephalosporin having the $R_2$, $R_3$ and $R_4$ substituents as they existed in the penicillin sulfoxide starting material. Illustrative of this is the situation in which $R_3$ is hydrogen and $R_4$ is α-aminophenylacetyl. In this instance the α-amino group would be silylated during formation of the silyl ester intermediate. Upon subsequent ring closure this silyl group would be cleaved to regenerate in the thus-formed cephalosporin an α-aminophenylacetyl group at the nitrogen in the 7-position. In view of the above, the definitions of $R_2$ and $R_4$ with respect to the penicillin sulfoxide and the silyl ester intermediate will in general correspond except in those instances in which the starting pencillin sulfoxide contains groups which can be silylated. As to such groups, $R_2$ and $R_4$ in the definition of the silyl ester intermediates is modified to account for the silylation effect.

When $R_3$ and $R_4$ are taken together with the nitrogen atom to which they are bonded, representative examples of the combination include, for example, phthalimido, succinimido, 2,2-dimethyl-5-oxo-4-phenylimidazolidin-1-yl, and the like.

The prior art describes literally thousands of penicillin compounds which, by the process of this invention, can be converted to desacetoxycephalosporin compounds. Any of the penicillin sulfoxides which are employed as starting materials in the process of this invention are readily available by techniques known in the art. For example, pencillin G (benzylpenicillin) or penicillin V (phenoxymethylpenicillin) can be converted to their corresponding sulfoxides and these used as starting materials in the process of this invention. Both penicillin G and pencillin V are available either naturally or biosynthetically, and both can be readily cleaved to produce 6-APA. 6-APA can itself be oxidized and thereby employed as starting material in this invention. 6-APA also can be modified by acylation in the 6-position and/or estification in the 3-position according to known techniques, thereby to produce any of the basic penicillin structures, which, in turn, can be oxidized in accordance with prior art techniques to produce the pencillin sulfoxides employed herein as starting materials.

Desacetoxycephalosporin compounds which are produced by the process of this invention from the corresponding penicillin sulfoxides, upon removal of any carboxy and/or other protecting group which might be present, are useful as antibiotics in therapeutic treatment of diseases caused by various Gram-positive and Gram-negative microorganisms. 7-Aminodesacetoxycephalosporanic acid (7-ADCA), produced from 6-APA sulfoxide by the process of this invention, is additionally usful as an intermediate to prepare other desacetoxycephalosporin antibiotic substances. Furthermore, any of the desacetoxycephalosporin products can be cleaved to produce 7-ADCA. The thus-obtained 7-ADCA can then be acylated, for example, with 2-thiopheneacetyl chloride to obtain 7-(2-thienyl)acetamido-3-methyl-3-cephem-4-carboxylic acid, a known antibiotic.

Illustrative of the silyl ester intermediates of this invention are the following:

Trimethylsilyl 3-phthalimido-4-oxo-1-(1'-methoxycarbonyl-2'-methyl-2'-propenyl)azetidine-2-sulfenate.

Trimethylsilyl 3-phthalimido-4-oxo-1-(1'-trimethylsilyloxycarbonyl-2'-methyl-2'-propenyl)azetidine-2-sulfenate.

Trimethylsilyl 3-phenoxyacetamido-4-oxo-1-(1'-p-nitrobenzyloxycarbonyl-2'-methyl-2'-propenyl)azetidine-2-sulfenate.

Triethylsilyl 3-phenylacetamido-4-oxo-1-[1'-(2,2,2-trichloroethoxycarbonyl)-2'-methyl-2'-propenyl]azetidine-2-sulfenate.

Trimethylsilyl 3-trimethylsilylamino-4-oxo-1-(1'-trimethylsilyloxycarbonyl-2'-methyl-2'-propenyl)azetidine-2-sulfenate.

Trimethylsilyl 3-(α-trimethylsilylaminophenylacetamido)-4-oxo-1-(1'-p-nitrobenzyloxycarbonyl-2'-methyl-2'-propenyl)azetidine-2-sulfenate.

Trimethylsilyl 3-(2'-thienyl)acetamido-4-oxo-1-(1'-benzyhydryloxycarbonyl-2'-methyl-2'-propenyl)azetidine-2-sulfenate.

Tributylsilyl 3-(4'-hydroxyphenyl)acetamido-4-oxo-1-(1'-benzyloxycarbonyl-2'-methyl-2'-propenyl)azetidine-2-sulfenate.

Triphenylsilyl 3-succinimido-4-oxo-1-[1'-(2-iodo)-ethyloxycarbonyl-2'-methyl-2'-propenyl]azetidine-2-sulfenate.

Trimethylsilyl 3-(3'-sydnone)acetamido-4-oxo-1-(1'-t-butoxycarbonyl-2'-methyl-2'-propenyl)azetidine-2-sulfenate.

Trimethylsilyl 3-(α-trimethylsilyloxyphenylacetamido)-4-oxo-1-(1'-p-hydroxybenzyloxycarbonyl-2'-methyl-2'-propenyl)azetidine-2-sulfenate.

Trimethylsilyl 3-(2',2'-dimethyl-3'-trimethylsilyl-5'-oxo-4'-phenylimidazolidin-1'-yl)-4-oxo-1-(1'-triphenylsilyloxycarbonyl-2'-methyl-2'-propenyl)azetidine-2-sulfenate.

Trimethylsilyl 3-(2'-furyl)acetamido-4-oxo-1-[1'-(9-fluorenyloxycarbonyl)-2'-methyl-2'-propenyl]azetidine-2-sulfenate.

Triethylsilyl 3-(4'-chlorophenyl)acetamido-4-oxo-1-(1'-p-methoxybenzyloxycarbonyl-2'-methyl-2'-propenyl)azetidine-2-sulfenate.

Trimethylsilyl 3-formamido-4-oxo-1-(1'-phthalimidomethoxycarbonyl-2'-methyl-2'-propenyl)azetidine-2-sulfenate.

Tripropylsilyl 3-(α-benzyloxycarbamido)phenylacetyl-4-oxo-1-(1'-p-methoxybenzyloxycarbonyl-2'-methyl-2'-propenyl)azetidine-2-sulfonate.

Trimethylsilyl 3-(3'-tolyl)acetamido-4-oxo-(1'-tetrahydropyranyloxycarbonyl-2'-methyl-2'-propenyl)azetidine-2-sulfenate.

Trimethylsilyl 3-thiophenoxyacetamido-4-oxo-1-(1'-benzhydryloxycarbonyl-2'-methyl-2'-propenyl)azetidine-2-sulfenate.

Trimethylsilyl 3-(2'-pyrrolyl)acetamido-4-oxo-1-(1'-ethoxycarbonyl-2'-methyl-2'-propenyl)azetidine-2-sulfenate.

Trimethylsilyl 3-(3'-thienyl)acetamido-4-oxo-1-(1'-benzyloxycarbonyl-2'-methyl-2'-propenyl)azetidine-2-sulfenate.

Trimethylsilyl 3-[2'-(1H-tetrazol-1-yl)acetamido]-4-oxo-1-(1'-p-nitrobenzyloxycarbonyl-2'-methyl-2'-propenyl)-azetidine-2-sulfenate.

Typical conversions of penicillin sulfoxides to desacetoxycephalosporins in accordance with the process of this invention include the following:

p-Nitrobenzyl 6-phenoxyacetamido-2,2-dimethylpenam-1-oxide-3-carboxylate to obtain p-nitrobenzyl 7-phenoxyacetamido-3-methyl-3-cephem-4-carboxylate.

t-Butyl 6-(2-thienyl)acetamido-2,2-dimethylpenam-1-oxide-3-carboxylate to obtain t-butyl 7-(2-thienyl)-acetamido-3-methyl-3-cephem-4-carboxylate.

2,2,2-Trichloroethyl 6-α-aminophenylacetamido-2,2-dimethylpenam-1-oxide-3-carboxylate to obtain 2,2,2-trichloroethyl 7-α-aminophenylacetamido-3-methyl-3-cephem-4-carboxylate.

p-Nitrobenzyl 6-(2',2'-dimethyl-5'-oxo-4'-phenylimidazolidin-1'-yl)-2,2-dimethylpenam-1-oxide-3-carboxylate to obtain p-nitrobenzyl 7-(2',2'-dimethyl-5'-oxo-4'-phenylimidazolidin-1'-yl)-3-methyl-3-cephem-4-carboxylate.

Benzhydryl 6-(α-formyloxy)phenylacetamido-2,2-dimethylpenam-1-oxide-3-carboxylate to obtain benzhydryl 7-(α-formyloxy)phenylacetamido-3-methyl-3-cephem-4-carboxylate.

Benzyl 6-(3-sydnone)acetamido-2,2-dimethylpenam-1-oxide-3-carboxylate to obtain benzyl 7-(3-sydnone)acetamido-3-methyl-3-cephem-4-carboxylate.

2-Iodomethyl 6-[2-(1H-tetrazol-1-yl]acetamido-2,2-dimethylpenam-1-oxide-3-carboxylate to obtain 2-iodomethyl 7-[2-(1H-tetrazol-1-yl)]acetamido-3-methyl-3-cephem-4-carboxylate.

6-Amino-2,2-dimethylpenam-1-oxide-3-carboxylic acid to obtain 7-amino-3-methyl-3-cephem-4-carboxylic acid.

Triphenylmethyl 6-succinimido-2,2-dimethylpenam-1-oxide-3-carboxylate to obtain triphenylmethyl 7-succinimido-3-methyl-3-cephem-4-carboxylate.

Trimethylsilyl 6-thiophenoxyacetamido-2,2-dimethylpenam-1-oxide-3-carboxylate to obtain 7-thiophenoxyacetamido-3-methyl-3-cephem-4-carboxylic acid.

Methyl 6-(2-furyl)acetamido-2,2-dimethylpenam-1-oxide-3-carboxylate to obtain methyl 7-(2-furyl)acetamido-3-methyl-3-cephem-4-carboxylate.

p-Nitrobenzyl 6-(N-trimethylsilyl)amino-2,2-dimethylpenam-1-oxide-3-carboxylate to obtain p-nitrobenzyl 7-amino-3-methyl-3-cephem-4-carboxylate.

Benzhydryl 6-phenylacetamido-2,2-dimethylpenam-1-oxide-3-carboxylate to obtain benzhydryl 7-phenylacetamido-3-methyl-3-cephem-4-carboxylate.

Benzyl 6-(2-nitrophenyl)sulfenamide-2,2-dimethylpenam-1-oxide-3-carboxylate to obtain benzyl 7-(2-nitrophenyl)sulfenamide-3-methyl-3-cephem-4-carboxylate.

p-Nitrobenzyl 6-(2-nitro-4-methoxyphenyl)sulfenamide-2,2-dimethylpenam-1-oxide-3-carboxylate to obtain p-nitrobenzyl 7-(2-nitro-4-methoxyphenyl)sulfenamide-3-methyl-3-cephem-4-carboxylate.

This invention is further illustrated by the following detailed examples.

EXAMPLE 1

Into a 50 ml., 3-neck flask was placed 752 mg. (2 millimoles) of methyl 6-phthalimido-2,2-dimethylpenam-1-oxide-3-carboxylate. To the flask were then added 10 ml. of benzene, 0.26 ml. (2 millimoles) of trimethylchlorosilane, and 0.21 ml. (1 millimole) of hexamethyldisilazane. The resulting mixture was stirred and refluxed for about 16 hours at 78°–80° C. The reaction mixture was then evaporated in vacuo to produce a residue of approximately a quantitative yield of trimethylsilyl 3-phthalimido-4-oxo-1-(1'-methoxycarbonyl-2'-methyl-2'-propenyl)azetidine-2-sulfenate.

Analysis, Calc. for $C_{20}H_{24}N_2O_6Si$: C, 53.57; H, 5.39; N, 6.25: Found: C, 53.76; H, 5.55; N, 6.42.

$[\delta]_D^{27}$ −164.4° (Benzene) $UV_{max}$ 220 mµ ($\xi$=47,200) 291 mµ ($\xi$=10,500) IR 2990, 2920, 1770, 1735, 1715, 1390, 1245, 874, 845 and 705 cm$^{-1}$.

NMR ($\delta$) 0.05 (s, 9H), 2.04 (s, 3H), 3.84 (s, 3H), 5.07 (two overlapping s), 5.20 (6s, 1H), 5.84 (s, AB, 2H), 7.86 (m, 4H).

MS m/e 448, 433, 359, 327, 299, 293, 262, 239, 204, 187, 172, 160, 113, 104, 89, 73.

EXAMPLE 2

To a suspension of 376 mg. of methyl 6-phthalimido-2,2-dimethylpenan-1-oxide-3-carboxylate in 10 ml. of benzene was added 0.25 ml. of N,O-bis(trimethylsilyl)acetamide. The resulting mixture was heated to reflux (about 78° C.) for about 22 hours. The reaction mixture was cooled to room temperature and evaporated in vacuo to produce a brown gum which exhibited an NMR spectrum consistent for the expected trimethylsilyl ester intermediate.

EXAMPLE 3

To a 50 ml., 3-neck flask was added 752 mg. (2 millimoles) of methyl 6-phthalimido-2,2-dimethylpenam-1-oxide-3-carboxylate in 10 ml. of benzene. To the resulting mixture was added 0.26 ml. (2 millimoles) of trimethylchlorosilane and 0.21 ml. (1 millimole) of hexamethyldisilazane. The resulting mixture was refluxed overnight after which the mixture was cooled to room temperature and evaporated in vacuo to produce a clear very viscous liquid. IR analysis established the presence of a β-lactam ring. MS analysis indicated the following m/e values: 448, 433, 389, 327, 359, 299, 293, 262, 239, 294, 204, 187, 172, 160, 152, 130, 120, 113, 104, 89 and 73. NMR analysis was consistent for the expected trimethylsilyl ester intermediate.

A sample of the above trimethylsilyl ester intermediate was treated with one equivalent of methanesulfonic acid in a 1:1 volume mixture of benzene and dimethylacetamide. The mixture was permitted to stand at room temperature overnight. The reaction mixture was then evaporated to dryness in vacuo at about 55° C. The residue was dissolved in a small amount of benzene and placed on a 1.5×21 cm. silica gel column. The sample was eluted from the column using 100 ml. quantities of benzene, 5% ethyl acetate in benzene, 10% ethyl acetate in benzene, and 15% ethyl acetate in benzene. Fractions of 20 ml. each were collected. Methyl 7-phthalimido-3-methyl-3-cephem-4-carboxylate in a yield of about 50% was obtained from fractions 7, 8, 9, and 10.

Analysis: NMR (CDCl$_3$) ($\delta$) 2.34 (s, 3H), 3.39 (d, J=16 and 47, 2H), 3.85 (s, 3H), 5.12 (d, J=4.5, 1H), 5.42 (d, J=4.5, 1H), and 7.82 (m, 4H).

IR (CHCl$_3$) 3020, 2970, 1800, 1785, 1725, 1390, 1220, 1110, and 907 cm$^{-1}$.

EXAMPLE 4

A mixture of 752 mg. (2 millimoles) of methyl 6-phthalimido-2,2-dimethylpenam-1-oxide-3-carboxylate, (393 mg. (3 millimoles) of N-trimethylsilylacetamide, and 10 ml. of benzene was refluxed (78° C.) for about 16 hours. The reaction mixture was then cooled to room temperature and evaporated in vacuo to a glassy solid residue. NMR of the residue was consistent for the trimethylsilyl ester intermediate.

The residue was re-dissolved in 10 ml. of benzene, and 20 mg. (0.2 millimole) of methanesulfonic acid dissolved in 2 ml. of a 60:40 mixture of dimethylacetamide and benzene was added. The resulting mixture was stirred at room temperature for about 16 hours. Thin-layer chromatography (TLC) of the reaction mixture showed the presence of a major amount (estimated greater than 70%) of methyl 7-phthalimido-3-methyl-3-cephem-4-carboxylate.

EXAMPLE 5

Into a 50 ml. 3-neck flask were placed 994 mg. (2 millimoles) of p-nitrobenzyl 6-phthalimido-2,2-dimethylpenam-1-oxide-3-carboxylate, 10 ml. of benzene, 0.26 ml. (2 millimoles) of trimethylchlorosilane, and 0.21 ml. (1 millimole) of hexamethyldisilazane. The mixture was heated to reflux (78°–80° C.) with stirring for about 16 hours. A small amount of solid formed in the reaction mixture and was filtered off. The filtrate was evaporated to dryness in vacuo to recover a yellow gum which by IR and NMR analysis was shown to be trimethylsilyl 3-phthalimido-4-oxo-1-(1'-p-nitrobenzyloxycarbonyl-2'-methyl-2'-propenyl)azetidine-2-sulfenate.

NMR (CDCl$_3$) ($\delta$) 0.05 (s, 9H), 2.09 (s, 3H), 5.14 (s, 1H), 5.33 (two overlapping s, 2H), 5.37 (s, 2H), 5.97 (s, 2H), 7.86 (s, 4H), 7.91 (q, 4H, J=90 and 40).

IR (CHCl$_3$) 3050, 2960, 1840, 1785, 1725, 1640, 1500, 1100, and 846 cm$^{-1}$.

EXAMPLE 6

To 50 ml. of benzene were added 1.75 grams (5 millimoles) 6-phthalimido-2,2-dimethylpenam-1-oxide-3-carboxylic acid, 1.3 ml. (10 millimoles) of trimethylchlorosilane, and 1.05 ml. (5 millimoles) of hexamethyldisilazane. The mixture was refluxed (78°–80° C.) for about 4.5 hours. The reaction mixture was then cooled to room temperature and evaporated in vacuo to produce a residue of trimethylsilyl 3-phthalimido-4-oxo-1-(1'-trimethylsilyloxycarbonyl-2'-methyl-2'-propenyl)azetidine-2-sulfenate in approximately quantitative yield.

Analysis, Calc.: for C$_{22}$H$_{30}$N$_2$O$_6$Si$_2$; C, 52.15; H, 5.97; N, 5.53; S, 6.32; Found: C, 51.98; H, 5.85; N, 5.58; S, 6.18.

[$\delta$]$_D^{27}$ −45.5° (Benzene)

IR (CDCl$_3$) 3010, 2960, 1795, 1775, 1740, 1725, 1382, 1250, 1063, 844, and 707 cm$^{-1}$.

NMR (CDCl$_3$) ($\delta$) 0.05 (s, 9H), 0.37 (s, 9H), 2.05 (s, 3H), 5.01 (s, 1H), 5.12 (s, 1H), 5.20 (s, 1H), 5.84 (s, AB pattern, 2H), and 7.84 (m, 4H).

MS m/e 506, 491, 416, 401, 388, 300, 299, 232, 230, 204, 187, 160, 147, 132, 114, 104, 73.

EXAMPLE 7

To a 250 ml., 3-neck flask were added 50 ml. of benzene, 2.6 grams (about 20 millimoles) of N-trimethylsilylacetamide, and 1.75 grams (5 millimoles) of 6-phthalimido-2,2-dimethylpenam-1-oxide-3carboxylic acid. The mixture was stirred for about 5 minutes, after which solution was about complete. The mixture was then heated slowly to reflux (about 80° C.) and maintained thereat for about 5 hours. The mixture was then cooled to room temperature, during which time a minor amount of solid crystallized out. The solid was filtered, and the filtrate was evaporated to dryness in vacuo to produce a residue confirmed by NMR analysis to be trimethylsilyl 3-phthalimido-4-oxo-1-(1'-trimethylsilyloxycarbonyl-2'-methyl-2'-propenyl)azetidine-2-sulfenate.

EXAMPLE 8

To a solution of 380 mg. (1 millimole) of methyl 6-phenoxyacetamido-2,2-dimethylpenam-1-oxide-3-carboxylate in 15 ml. of dry toluene maintained at 40° C. were added 330 mg. (about 2 millimoles) of N-trimethylsilylacetamide and 0.023 ml. (about 0.2 millimole) of trimethylchlorosilane. The resulting mixture was refluxed at about 111° C. for about 5 hours. The reaction mixture was then cooled to room temperature and evaporated in vacuo to a brown gummy solid residue. NMR analysis established that the residue contained trimethylsilyl 3-phenoxyacetamido-4-oxo-1-(1'-methoxycarbonyl-2'-methyl-2'-propenyl)-azetidine-2-sulfenate.

NMR (CDCl$_3$) 0.05 (s, 9H), 2.04 (s, 3H), 3.75 (s, 3H), 4.54 (s, 2H), 5.07 (s, 2H), 5.47 (s, 1H), 5.67 (q, J=4.5 and 8.0, 1H), 6.17 (d, J=4.5, 1H), 7.85 (d, J=8.0, 1H).

EXAMPLE 9

To a solvent mixture of 25 ml. of 60% toluene and 40% acetonitrile were added 1.25 grams (2.5 millimoles) of p-nitrobenzyl 6-phenoxyacetamido-2,2-dimethylpenam-1-oxide-3-carboxylate, 1.0 gram (7.5 millimoles) of N-trimethylsilylacetamide, and 0.19 ml. (1.5 millimoles) of trimethylchlorosilane. The mixture was heated to reflux (about 87° C.) and maintained thereat for about 20 hours. The mixture was then cooled to room temperature, and about 0.17 ml. of methanesulfonic acid was added. The mixture was then stirred at room temperature for about 16 hours. A minor amount of solid formed in the mixture. The solid was removed by filtration, and the filtrate was shown by thin-layer chromatography (TLC) to contain principally p-nitrobenzyl 7-phenoxyacetamido-3-methyl-3-cephem-4-carboxylate.

EXAMPLE 10

To a mixture of 25 ml. of benzene and 18 ml. of dimethylacetamide were added 2.5 grams (5 millimoles) of p-nitrobenzyl 6-phenoxyacetamido-2,2-dimethylpenam-1-oxide-3-carboxylate, 2 grams (about 15 millimoles) of N-trimethylsilylacetamide, and 0.19 ml. (1.5 millimoles) of trimethylchlorosilane. The resulting mixture was heated to reflux (91° C.). The mixture was refluxed for about 20 hours, after which time it was cooled to room temperature and 0.11 ml. of methanesulfonic acid was added. The mixture was then stirred at room temperature for about 16 hours. The reaction mixture was then evaporated in vacuo to a residue. The residue was dissolved in 20 ml. of benzene. A minor amount of insoluble crystalline material remained which was filtered off. The filtrate was then passed onto a silica gel chromatographic column, and the sample eluted therefrom using successively 200 ml. of 5% ethyl acetate in benzene, 1000 ml. of 10% ethyl acetate in benzene, and 400 ml. of 15% ethyl acetate in benzene to recover p-nitrobenzyl 7-phenoxyacetamido-3-methyl-3-cephem-4-carboxylate.

EXAMPLE 11

Into a 250 ml. 3-neck flask were placed 25 ml. of dimethylacetamide, 62.5 ml. of dry toluene, 1.84 grams (14 millimoles) of N-trimethylsilylacetamide, and 0.091 ml. (1.4 millimoles) of methanesulfonic acid. To the resulting mixture was added 5.0 grams (10 millimoles) of p-nitrobenzyl 6-phenoxyacetamido-2,2-dimethylpenam-1-oxide-3-carboxylate. The mixture was refluxed (115° C.) for about 1.5 hours, after which the resulting dark red solution was evaporated in vacuo to a residue of about 10 grams. The residue was cooled and seeded with a small amount of p-nitrobenzyl 7-phenoxyacetamido-3-methyl-3-cephem-4-carboxylate, after which crystallization began. Ethanol (50 ml.) was slowly added to complete crystallization of the product. The solid was filtered, washed with ethanol, and vacuum-dried to yield 2.6 grams of p-nitrobenzyl 7-phenoxyacetamido-3-methyl-3-cephem-4-carboxylate.

EXAMPLE 12

To a mixture of 25 ml. of dimethylacetamide and 62 ml. of dry toluene were added 1.31 grams (10 millimoles) of N-trimethhylsilylacetamide and 5.0 grams (10 millimoles) of p-nitrobenzyl 6-phenoxyacetamido-2,2-dimethylpenam-1-oxide-3-carboxylate. The mixture was refluxed at 118° C. for about 0.5 hour, after which the resulting light brown solution was cooled to about 80° C. and 0.065 ml. (1 millimole) of methanesulfonic acid was added. The mixture was then refluxed at 118° C. for an additional one hour. The brown solution was evaporated in vacuo to a residue of about 10 grams. The residue was cooled and seeded, after which crystallization began to occur. About 50 ml. of ethanol was slowly added, and the resulting mixture was filtered. The solid was washed with additional ethanol and vacuum-dried overnight at 40° C. to yield 2.0 grams of p-nitrobenzyl 7-phenoxyacetamido-3-methyl-3-cephem-4-carboxylate.

EXAMPLE 13

To a mixture of 50 ml. of benzene and 37.5 ml. of dimethylacetamide was added 5.0 grams (10 millimoles) of p-nitrobenzyl 6-phenoxyacetamido-2,2-dimethylpenam-1-oxide-3-carboxylate. To the resulting solution were then added 1.26 ml. (10 millimoles) of trimethylchlorosilane and 1.05 ml. (5 millimoles) of hexamethyldisilazine. The mixture was refluxed at 95° C. for 14.5 hours, and the resulting dark red mixture was then cooled to room temperature. To the mixture was then added 0.058 ml. (0.9 millimole) of methanesulfonic acid. The mixture was stirred for 15 minutes at about 30° C. and then stirred for about 100 minutes at 55° C. The reaction mixture was then evaporated to near dryness and 10 ml. of ethanol was added. Crystals began to form after about one hour, at which time an additional 30 ml. of ethanol was added. The mixture was refrigerated for three days, and the crystals were filtered. The crystals were re-dissolved in 5 ml. of dioxane to which was then added 15 ml. of ethanol. Crystals began slowly to form. The crystals were filtered, washed with ethanol and dried to yield 550 mg. of p-nitrobenzyl 7-phenoxyacetamido-3-methyl-3-cephem-4-carboxylate.

EXAMPLE 14

A mixture of 5.0 grams (10 millimoles) of p-nitrobenzyl 6-phenoxyacetamido-2,2-dimethylpenam-1-oxide-3-carboxylate in 60 ml. of dioxane was prepared and warmed to about 40° C. To this warmed mixture were added 1.26 ml. (10 millimoles) of hexamethyldisilazane. The resulting mixture was heated slowly to a temperature of 100° C. and maintained thereat for about 5 hours during which time it turned from a light yellow solution fo a light brown solution.

The mixture was then cooled to about 40° C. and 0.04 ml. of boron trifluoride etherate was added. The solution turned slightly red and stirring at room temperature was continued for about 16 hours. The reaction mixture was then evaporated to near dryness in a rotary evaporator. The residue was recrystallized from 20 ml. of a 1:3 mixture of dioxane and ethanol containing about 1 ml. of dimethylacetamide to produce p-nitrobenzyl 7-phenoxyacetamido-3-methyl-3-cephem-carboxylate.

EXAMPLE 15

To a mixture of 25 ml. of benzene and 19 ml. of dimethylacetamide were added 2.45 grams (5 millimoles) of 2,2,2-trichloroethyl 6-phenoxyacetamido-2,2-dimethylpenam-1-oxide-3-carboxylate, 1.7 grams (about 10 millimoles) of N-trimethylsilylacetamide and 0.035 ml. (0.5 millimole) of methanesulfonic acid. The mixture was refluxed at 95°–96° C. for 15.5 hours. The reaction mixture was then extracted three times with water, and the benzene layer was dried over magnesium sulfate. NMR and TLC analyses established the structure of the product present in the benzene layer to be 2,2,2-trichloroethyl 7-phenoxyacetamido-3-methyl-3-cephem-4-carboxylate.

NMR (CDCl$_3$) ($\delta$) 2.20 (s, 3H), 3.20 and 3.57 (2d, 2H), 4.55 (s, 2H), 4.87 (d, 2H), 5.03 (d, J=4.5, 1H), 5.83 (d, J=4.5 and 8.0, 1H), 6.80–7.40 (m, 5H), 7.94 (d, J=8.0, 1H).

EXAMPLE 16

A solution of 1.41 grams (3 millimoles) of p-nitrobenzyl 6-phenylacetamido-2,2-dimethylpenam-1-oxide-3-carboxylate in 30 ml. of dioxane was prepared. To the resulting solution were added 17 ml. of dry benzene followed by 730 mg. (4.5 millimoles) of N-trimethylsilylacetamide and 0.06 ml. of trimethylchlorosilane. The resulting mixture was refluxed at 84° C. for 16 hours. The reaction mixture, a light yellow, clear solution, was cooled to about 50° C., and 0.002 ml. of methanesulfonic acid was added. The mixture was then maintained at about 50° C., stirred for two hours, and then evaporated to dryness in vacuo. The residue, unable to be recrystallized from ethanol, remained in the form of a gum which, by TLC analysis, was shown to contain p-nitrobenzyl 7-phenylacetamido-3-methyl-3-cephem-4-carboxylate.

EXAMPLE 17

To 20 ml. of dioxane was added 700 mg. (3 millimoles) of 6-aminopenicillanic acid sulfoxide, and the resulting mixture was warmed to about 60° C. A tiny drop of trifluoroacetic acid was added followed by 1.3 grams (about 10 millimoles) of N-trimethylsilylacetamide, the trifluoroacetic acid being added to neutralize a trace of triethylamine impurity present in the N-trimethylsilylacetamide. The mixture was heated to reflux for about 3 hours, during which time the mixture turned to a red-brown color but remained clear. The mixture was then evaporated to dryness in vacuo to produce a red-brown gum.

The gum was dissolved in 20 ml. of dry benzene, and 0.02 ml. of methanesulfonic acid was added and the mixture stirred at 50° C. for 2.5 hours. The mixture was cooled to room temperature and 10 ml. of methanol was added dropwise followed by 5.0 ml. of water. A solid precipitated from the mixture, and the mixture was stirred for about 20 minutes, filtered, and the filtrate was evaporated under vacuum. The residue was then suspended in water, and aqueous sodium bicarbonate solution was added to pH 8.0. The solid dissolved at this pH, and the pH was then adjusted to 3.5 by addition of acid, and a precipitate formed. The precipitate was filtered, and dried in vacuo to give 40 mg. of a material established by TLC, IR, and UV to be 7-amino-3-methyl-3-cephem-4-carboxylic acid.

IR (mull) 2960, 2870, 1800, 1620, 1530, 1350, 795, and 786 cm$^{-1}$.

UV$_{max}$ (pH 6.8 buffer) 262 m$\mu$ ($\xi$=72,200) 245 m$\mu$ ($\xi$=62,500).

EXAMPLE 18

To about 100 ml. of toluene were added 3.82 grams of 6-phenoxyacetamido-2,2-dimethylpenam-1-oxide-3-carboxylic acid, about 4 grams of N-trimethylsilylacetamide, and 0.07 ml. of methanesulfonic acid. The mixture was refluxed at 111° C. for about 16 hours. To the tarry dark brown reaction mixture 30 ml. of methanol was added. A TLC of the reaction mixture indicated the presence of 7-phenoxyacetamido-3-methyl-3-cephem-4-carboxylic acid. The reaction mixture was evaporated to dryness in vacuo, and 25 ml. of acetonitrile was added to the residue. Insolubles were filtered off, and the filtrate was evaporated in vacuo. About 25 ml. of ethyl acetate was added to the residue. The ethyl acetate solution was extracted with 25 ml. of saturated aqueous sodium bicarbonate. The aqueous layer was then separated, washed with 25 ml. of ethyl acetate, separated, and slurried with an additional 25 ml. of ethyl acetate. The pH of the resulting mixture was adjusted to about 3.3 by addition of concentrated HCl. The aqueous layer was separated from the ethyl acetate layer, and the ethyl acetate layer was washed with 25 ml. of water. The ethyl acetate was then extracted with 25 ml. of saturated aqueous sodium bicarbonate. The aqueous sodium bicarbonate was washed twice with 25 ml. of ethyl acetate and then slurried with an additional 25 ml. of ethyl acetate and the pH adjusted to about 2.5 by addition of concentrated HCl. The ethyl acetate layer was separated and washed with 25 ml. of water. Activated charcoal and MgSO$_4$ was added to the ethyl acetate layer; the mixture was stirred for about 30 minutes and filtered. The filtrate was evaporated to about 20 ml., seeded, and refrigerated to produce crystalline 7-phenoxyacetamido-3-methyl-3-cephem-4-carboxylic acid.

I claim:

1. A compound of the formula

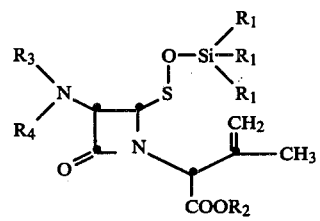

in which each $R_1$ independently is $C_1$–$C_4$ alkyl or phenyl; $R_2$ is $C_1$–$C_6$ alkyl, 2,2,2-trihaloethyl, 2-iodoethyl, benzyl, nitrobenzyl, tetrahydropyranyl, 9-fluorenyl, succinimidomethyl, phthalimidomethyl, methoxybenzyl, dimethoxybenzyl, cyanomethyl, nitrophenyl, dinitrophenyl, 2,4,6-trinitrophenyl, bis(p-methoxyphenyl)methyl, triphenylmethyl, benzhydryl, benzyloxymethyl, $C_2$–$C_6$ alkanoyloxymethyl, $C_2$–$C_4$ alkanoyl, phenacyl, or a radical of the formula

in which each $R_1$ is as herein defined; $R_3$ is hydrogen and $R_4$ is $C_1$–$C_8$ alkanoyl; azidoacetyl; cyanoacetyl; haloacetyl;

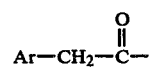

in which Ar is phenyl, thienyl, furyl, pyrrolyl, or phenyl substituted with from one to three substituents selected from the group consisting of fluorine, chlorine, bromine, iodine, trifluoromethyl, $C_1$–$C_3$ acyloxy, -OSi($R_1$)$_3$ in which $R_1$ is as herein defined, $C_1$–$C_3$ alkyl, $C_1$–$C_3$ alkoxy, cyano, and nitro;

in which Ar' is phenyl, pyridyl, or substituted phenyl as defined above, and Y is oxygen or sulfur;

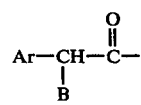

in which Ar is as defined above, and B is $C_1$–$C_3$ acyloxy,

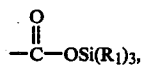

esterified carboxyl, -CN, -N$_3$, or -NMR in which R is benzyloxycarbonyl, C$_1$-C$_4$ alkoxycarbonyl, cycloalkoxycarbonyl, triphenylmethyl,

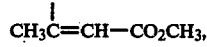

2,2,2-trichloroethoxycarbonyl, or -Si(R$_1$)$_3$ in which R$_1$ is as herein defined; (3-sydnone) C$_2$-C$_3$ alkanoyl;

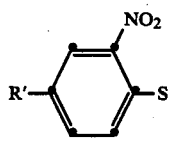

in which R' is hydrogen or methoxy; 2-(1H-tetrazol-1-yl)acetyl; or R$_3$ and R$_4$ taken together with the nitrogen atom to which they are bonded are phthalimido, a cyclic imide moiety of a C$_3$-C$_{12}$ dicarboxylic acid, or 2,2-dimethyl-5-oxo-4-phenylimidazolidin-1-yl.

2. Compound of claim 1, in which R$_1$ is methyl or phenyl; R$_2$ is C$_1$-C$_6$ alkyl, 2,2,2-trihaloethyl, benzyl, nitrobenzyl, methoxybenzyl, benzhydryl, C$_2$-C$_6$ alkanoyloxymethyl, phenacyl, or a radical of the formula

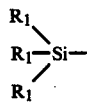

in which R$_1$ is methyl or phenyl; R$_3$ is hydrogen and R$_4$ is

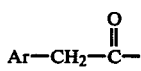

in which Ar is phenyl, thienyl, or phenyl substituted with from one to three substituents selected from the group consisting of fluorine, chlorine, bromine, iodine, trifluoromethyl, C$_1$-C$_3$ acyloxy, -OSi(R$_1$)$_3$, C$_1$-C$_3$ alkyl, C$_1$-C$_3$ alkoxy, cyano, and nitro;

in which Ar' is phenyl, or substituted phenyl as defined above, and Y is oxygen or sulfur;

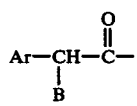

in which Ar is as defined above, and B is C$_1$-C$_3$ acyloxy,

or -NHR in which R is benzyloxycarbonyl, C$_1$-C$_4$ alkoxycarbonyl, cycloalkoxycarbonyl, triphenylmethyl,

2,2,2-trichloroethoxycarbonyl, or -Si(R$_1$)$_3$ in which R$_1$ is as herein defined;

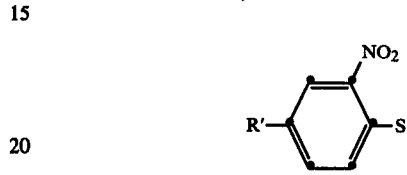

in which R' is hydrogen or methoxy; 2-(1H-tetrazol-1-yl)acetyl; or R$_3$ and R$_4$ taken together with the nitrogen atom to which they are bonded are phthalimido or 2,2-dimethyl-5-oxo-4-phenylimidazolidin-1-yl.

3. Compound of claim 1, in which R$_1$ is methyl; R$_2$ is C$_1$-C$_6$ alkyl, 2,2,2-trihaloethyl, benzyl, nitrobenzyl, methoxybenzyl, benzhydryl, phenacyl, or a radical of the formula (CH$_3$)$_3$Si-; R$_3$ is hydrogen and R$_4$ is

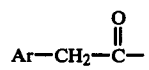

in which Ar is phenyl;

in which Ar' is phenyl, and Y is oxygen; or R$_3$ and R$_4$ taken together with the nitrogen atom to which they are bonded are 2,2-dimethyl-5-oxo-4-phenylimidazolidin-1-yl.

4. Compound of claim 1, in which R$_1$ is methyl.

5. Compound of claim 1, in which R$_2$ is t-butyl, 2,2,2-trichloroethyl, p-nitrobenzyl, benzyl, p-methoxybenzyl, benzhydryl, or trimethylsilyl.

6. Compound of claim 1, in which R$_3$ is hydrogen and R$_4$ is

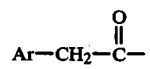

in which Ar is phenyl.

7. Compound of claim 1, in which R$_3$ is hydrogen and R$_4$ is

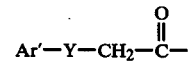

in which Ar' is phenyl and Y is oxygen.

8. Compound of claim 1, in which R$_3$ is hydrogen and R$_4$ is in which Ar is 2-thienyl.

9. Compound of claim 1, in which $R_3$ is hydrogen and $R_4$ is

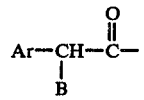

in which Ar is phenyl and B is -NHR.

10. Compound of claim 1, in which $R_2$ is benzyl, nitrobenzyl, methoxybenzyl, dimethoxybenzyl, or benzyloxymethyl, $R_3$ is hydrogen, and $R_4$ is

in which Ar' is phenyl or substituted phenyl and Y is oxygen or sulfur.

11. Compound of claim 1, in which $R_1$ is methyl, $R_2$ is p-nitrobenzyl, $R_3$ is hydrogen, and $R_4$ is

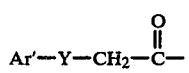

in which Ar' is phenyl and Y is oxygen.

12. Compound of claim 1, in which $R_2$ is -Si($R_1$)$_3$, $R_3$ is hydrogen, and $R_4$ is -Si($R_1$)$_3$.

13. Compound of claim 1, in which $R_2$ is -Si($R_1$)$_3$.

14. Compound of claim 1, in which $R_3$ is hydrogen and $R_4$ is -Si($R_1$)$_3$.

15. Compound of claim 1, in which $R_2$ is methyl, ethyl, n-propyl, isopropyl, n-butyl, sec-butyl, isobutyl, t-butyl, amyl, hexyl, 2,2,2-trichloroethyl, 2,2,2-tribromoethyl, 2-iodoethyl, benzyl, p-nitrobenzyl, tetrahydropyranyl, succinimidomethyl, phthalimidomethyl, p-methoxybenzyl, cyanomethyl, 3,4-dimethoxybenzyl, p-nitrophenyl, 2,4-dinitrophenyl, 2,4,6-trinitrophenyl, bis(p-methoxyphenyl)-methyl, triphenylmethyl, benzhydryl, benzyloxymethyl, acetoxymethyl, propionoxymethyl, acetyl, propionyl, or phenacyl.

16. Compound of claim 1, in which $R_3$ is hydrogen and $R_4$ is formyl, acetyl, propionyl, butyryl, valeryl, caproyl, azidoacetyl, cyanoacetyl, chloroacetyl, bromoacetyl, phenylacetyl, 2-thienylacetyl, 3-thienylacetyl, 2-furylacetyl, 3-furylacetyl, 2-pyrrolylacetyl, 3-pyrrolylacetyl, 4-chlorophenylacetyl, 3-trifluoromethylphenylacetyl, 4-hydroxyphenylacetyl, 3-tolylacetyl, 4-cumylacetyl, 4-methoxyphenylacetyl, 3-cyanophenylacetyl, 4-nitrophenylacetyl, phenoxyacetyl, thiophenylacetyl, pyridyloxyacetyl, p-nitrophenoxyacetyl, α-aminophenylacetyl, α-benzyloxycarbamidophenylacetyl, α-t-butoxycarbamidophenylacetyl, α-formyloxyphenylacetyl, α-cyanophenylacetyl, α-azidophenylacetyl, 3-sydnoneacetyl, 2-(1H-tetrazol-1-yl)acetyl, 2-nitrophenylthio, or 2-nitro-4-methoxyphenylthio.

17. Compound of claim 1, in which $R_3$ is hydrogen and $R_4$ is

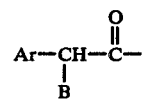

in which Ar is phenyl, B is -NHR, and R is -Si($R_1$)$_3$.

18. Compund of claim 1, in which $R_3$ and $R_4$ taken together with the nitrogen atom to which they are bonded are phthalimido, succinimido, or 2,2-dimethyl-5-oxo-4-phenylimidazolidin-1-yl.

19. Compound of claim 1, in which $R_1$ is ethyl, $R_2$ is 2,2,2-trichloroethyl, $R_3$ is hydrogen, and $R_4$ is

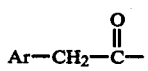

in which Ar is phenyl.

20. Compound of claim 12, in which $R_1$ is methyl.

21. Compound of claim 1, in which $R_1$ is methyl, $R_2$ is p-nitrobenzyl, $R_3$ is hydrogen, and $R_4$ is

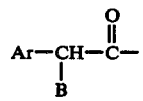

in which Ar is phenyl, B is -NHR and R is trimethylsilyl.

22. Compound of claim 1, in which $R_1$ is methyl, $R_2$ is 2,2,2-trichloroethyl, $R_3$ is hydrogen, and $R_4$ is

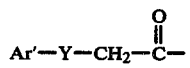

in which Ar' is phenyl and Y is oxygen.

23. Compound of claim 1, in which $R_1$ is methyl, $R_2$ is p-nitrobenzyl, $R_3$ is hydrogen, and $R_4$ is

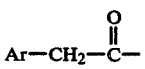

in which Ar is phenyl.

24. Compound of claim 1, in which $R_1$ is methyl, $R_2$ is -Si($R_1$)$_3$, $R_3$ is hydrogen, and $R_4$ is

in which Ar' is phenyl and Y is oxygen.

* * * * *

UNITED STATES PATENT AND TRADEMARK OFFICE
CERTIFICATE OF CORRECTION

PATENT NO. : 4,159,267
DATED : June 26, 1979
INVENTOR(S) : Ta-Sen Chou

It is certified that error appears in the above-identified patent and that said Letters Patent are hereby corrected as shown below:

Column 21, line 5, "-NMR" should read -- -NHR--.

Signed and Sealed this

Fourth Day of December 1979

[SEAL]

Attest:

SIDNEY A. DIAMOND

Attesting Officer

Commissioner of Patents and Trademarks